United States Patent [19]
Smith et al.

[11] Patent Number: 5,456,925
[45] Date of Patent: Oct. 10, 1995

[54] PHARMACEUTICAL COMPOSITIONS CONTAINING FURAN DERIVATIVES

[75] Inventors: Norman R. Smith, London; Colin R. Heppenstall, Bishops Stortford; Stephen J. Douglas, St. Albans, all of England

[73] Assignee: Glaxo Group Limited, Middlesex, United Kingdom

[21] Appl. No.: 215,658

[22] Filed: Mar. 22, 1994

Related U.S. Application Data

[63] Continuation of Ser. No. 898,834, Jun. 15, 1992, abandoned, which is a continuation of Ser. No. 757,285, Sep. 10, 1991, abandoned.

[30] Foreign Application Priority Data

Sep. 11, 1990 [GB] United Kingdom .................. 9019875

[51] Int. Cl.$^6$ .................. A61K 33/00; A61K 31/555; A61K 31/34; A61K 31/29
[52] U.S. Cl. .................. 424/715; 424/717; 514/184; 514/471; 514/503
[58] Field of Search .................. 424/717, 715; 514/471, 503, 184

[56] References Cited

U.S. PATENT DOCUMENTS

| | | | |
|---|---|---|---|
| 4,608,257 | 8/1986 | Teeter | 424/717 |
| 5,008,256 | 4/1991 | Clitherow | 514/184 |
| 5,013,560 | 5/1991 | Stentz et al. | 514/503 |
| 5,064,857 | 11/1991 | Bertholdt et al. | 514/503 |
| 5,102,665 | 4/1992 | Schaeffer | 424/43 |

OTHER PUBLICATIONS

Goodman et al., The Pharmacological Basis of Therapeutics, 7th edition (1986) pp. 980–987.

*Primary Examiner*—Raymond Henley, III
*Attorney, Agent, or Firm*—Bacon & Thomas

[57] ABSTRACT

The invention relates to a pharmaceutical composition in solid unit dosage form adapted for oral administration, comprising a salt formed between ranitidine and a complex of bismuth with a carboxylic acid selected from tartaric acid and citric acid together with an alkaline salt. For example the composition is in tablet form and comprises ranitidine bismuth citrate and sodium carbonate.

The composition shows improved disintegration and/or dissolution.

11 Claims, No Drawings

PHARMACEUTICAL COMPOSITIONS CONTAINING FURAN DERIVATIVES

This application is a Continuation of application Ser. No. 07/898,834, filed Jun. 15, 1992, now abandoned, which is a Continuation of application Ser. No. 07/757,285, filed Sep. 10, 1991, now abandoned.

The present invention relates to improvements in the formulation of derivatives of the $H_2$-receptor antagonist ranitidine, particularly for oral administration. More especially the invention is concerned with pharmaceutical compositions in which the active ingredient is a salt of ranitidine and a complex of bismuth with a carboxylic acid.

Published UK Patent Specification No. 2220937A describes and claims salts formed between ranitidine and a complex of bismuth with a carboxylic acid, particularly tartaric acid and, more especially, citric acid. Such salts possess the $H_2$-antagonist antisecretory properties associated with ranitidine, together with antibacterial activity against *Helicobacter pylori* (formerly *Campylobacter pylori*). In addition, such salts possess cytoprotective properties, and display activity against the human gastric pepsins, with preferential inhibition of pepsin 1, a pepsin isozyme associated with peptic ulcer.

The salts disclosed in UK Patent Specification No. 2220937A thus possess a particularly advantageous combination of properties for the treatment of gastrointestinal disorders, especially peptic ulcer disease and other gastroduodenal conditions, for example gastritis and non-ulcer dyspepsia.

UK Patent Specification No. 2220937 A also discloses pharmaceutical compositions containing salts formed between ranitidine and a complex of bismuth with a carboxylic acid. Such compositions are primarily intended for oral administration, and may take the form of for example tablets, capsules, solutions, syrups, suspensions or dry products for constitution with water or other suitable vehicle before use.

One of the important properties associated with pharmaceutical compositions in solid form for oral administration is that, once swallowed by the patient, they should disintegrate and/or dissolve in order to release the active ingredient. It has now been found that the rate of disintegration and/or dissolution of such compositions, in particular tablets, containing a salt of the type described in UK Patent Specification No. 2220937A as the active ingredient, may be significantly improved, particularly under acid conditions, by incorporating an alkaline salt into the formulation. This in turn serves to increase the extent to which the active ingredient is released from the composition.

Thus the present invention provides a pharmaceutical composition in solid unit dosage form for oral administration, comprising a salt formed between ranitidine and a complex of bismuth with a carboxylic acid selected from tartaric acid or citric acid, and an alkaline salt.

Compositions containing solvates, including hydrates, of the ranitidine salts are also included within the scope of the invention.

The salt of ranitidine may be for example N-[2-[[[5-[(dimethylamino)methyl]- 2-furanyl]methyl]thio]ethyl]-N'-methyl-2-nitro- 1,1-ethenediamine 2-hydroxy- 1,2,3-propanetricarboxylate bismuth ($3^+$) complex, also known as ranitidine bismuth citrate; or N-[2-[[[5-[(dimethylamino)methyl]-2-furanyl] methyl]thio]ethyl]-N'-methyl-2-nitro-1,1-ethenediamine [R-(R*R*)]-2,3-dihydroxybutanedioate bismuth ($3^+$) complex, also known as ranitidine bismuth tartrate. Such salts may be formed by reacting ranitidine with an appropriate bismuth carboxylic acid complex, e.g. bismuth citrate or bismuth tartrate.

Compositions containing ranitidine bismuth citrate as the active ingredient are particularly preferred.

The alkaline salt may be for example a carbonate, bicarbonate, citrate, phosphate or acetate salt. The use of an alkali metal (e.g. sodium or potassium) or alkaline earth metal (e.g. magnesium or calcium) carbonate or bicarbonate, or mixtures thereof is preferred. Sodium bicarbonate and/or sodium carbonate is particularly preferred, more especially sodium carbonate, which may conveniently be used in its anhydrous form. Examples of other suitable alkaline salts that may be used include ammonium carbonate sodium acetate, sodium citrate, potassium acetate, potasssium citrate and dipotassium phosphate.

The amount of ranitidine bismuth carboxylate in the composition according to the invention may be for example 150 mg to 1.5 g, preferably 200 to 800 mg.

The alkaline salt may constitute for example 2% to 20% of the composition on a weight-to-weight (w/w) basis, preferably 2% to 8%.

The ranitidine bismuth carboxylate content of the composition may be for example 20% to 95%, preferably 50% to 95%, more particularly 80% to 95%, on a w/w basis.

A preferred composition comprises ranitidine bismuth citrate and sodium carbonate.

The compositions according to the invention are intended for use in human or veterinary medicine.

The composition may be administered, for example, one to four times daily, preferably once or twice. The dosage will however depend on the nature and severity of the condition being treated, and it will also be appreciated that it may be necessary to make routine variations to the dosage depending on the age and weight of the patient.

The composition may take the form of for example tablets (including chewable tablets), capsules (of either the hard or soft type), powders or granules. Tablets are preferred.

The composition according to the invention may be formulated using additional physiologically acceptable carriers or excipients as appropriate. Such additional carriers or excipients may be for example binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. starch or sodium starch glycollate); or wetting agents (e.g. sodium lauryl sulphate). Tablets may be coated by methods well known in the art. The preparations may also contain flavouring, colouring and/or sweetening agents as appropriate.

Compositions according to the invention may be prepared according to conventional techniques well known in the pharmaceutical industry for the manufacture of solid dosage forms for oral administration. Thus the ranitidine bismuth carboxylate and alkaline salt may, for example, be blended with suitable excipients and, if desired, granulated. Tablets may be prepared, for example, by compression of the blend or granulate, using a lubricant as an aid to tabletting.

The following Examples illustrate tablets and capsules according to the invention in which the active ingredient is in particular ranitidine bismuth citrate.

Tablets may be film coated with suitable film forming materials, such as hydroxypropyl methylcellulose, using standard techniques.

| Example 1 | mg/tablet | | |
| --- | --- | --- | --- |
| Active ingredient | 200.0 | 400.0 | 800.0 |
| Anhydrous sodium carbonate USNF | 19.0 | 25.0 | 46.0 |
| Microcrystalline cellulose Ph. Eur. | 149.6 | 60.0 | 46.0 |
| Polyvinylpyrrolidone | 7.6 | 10.0 | 18.4 |
| Magnesium stearate Ph. Eur. | 3.8 | 5.0 | 9.2 |
| Compression weight | 380.0 | 500.0 | 919.6 |

The active ingredient, sodium carbonate and microcrystalline cellulose were blended together, granulated using a solution of the polyvinylpyrrolidone in isopropyl alcohol, and dried. The granule was blended with magnesium stearate and compressed into tablets using suitable punches.

| Example 2 | mg/tablet | |
| --- | --- | --- |
| Active ingredient | 400.0 | 400.0 |
| Sodium bicarbonate USNF | 85.0 | 21.7 |
| Polyvinylpyrrolidone | 10.0 | 8.7 |
| Magnesium stearate Ph. Eur. | 5.0 | 4.4 |
| Compression weight | 500.0 | 434.8 |

The active ingredient and sodium bicarbonate were blended together, granulated using a solution of the polyvinylpyrrolidone in isopropyl alcohol, and dried. The granule was blended with magnesium stearate and compressed into tablets using suitable punches.

| Example 3 | mg/tablets |
| --- | --- |
| Active ingredient | 400.0 |
| Anhydrous sodium carbonate USNF | 2.5 |
| Sodium bicarbonate USNF | 22.5 |
| Microcrystalline cellulose Ph. Eur. | 60.0 |
| Polyvinylpyrrolidone | 10.0 |
| Magnesium stearate Ph. Eur. | 5.0 |
| Compression weight | 500.0 |

Tablets were prepared according to the method described in Example 1, using the sodium carbonate and sodium bicarbonate in place of sodium carbonate alone.

| Example 4 | mg/tablets |
| --- | --- |
| Active ingredient | 600.0 |
| Anhydrous sodium carbonate USNF | 36.0 |
| Lactose | 60.0 |
| Polyvinylpyrrolidone | 15.0 |
| Magnesium stearate | 8.0 |
| Compression weight | 719.0 |

The active ingredient, sodium carbonate and lactose are blended together, granulated using a solution of the polyvinylpyrrolidone in ethyl alcohol, and dried. The granule is blended with magnesium stearate and compressed into tablets using suitable punches.

| Example 5 | mg/tablets |
| --- | --- |
| Active ingredient | 600.0 |
| Sodium bicarbonate USNF | 36.0 |
| Lactose | 60.0 |
| Polyvinylpyrrolidone | 15.0 |
| Magnesium stearate | 8.0 |
| Compression weight | 719.0 |

The active ingredient, sodium bicarbonate and lactose are blended together, granulated using a solution of the polyvinylpyrrolidone in isopropyl alcohol, and dried. The granule is blended with magnesium stearate and compressed into tablets using suitable punches.

| Example 6 | mg/capsule |
| --- | --- |
| Active ingredient | 400.0 |
| Anhydrous sodium carbonate USNF | 2.5 |
| Sodium bicarbonate USNF | 22.5 |
| Microcrystalline cellulose Ph. Eur. | 57.5 |
| Polyvinylpyrrolidone | 10.0 |
| Magnesium stearate | 5.0 |
| Silicon dioxide | 2.5 |
| Fill weight | 500.0 |

The active ingredient, sodium carbonate, sodium bicarbonate and microcrystalline cellulose are blended together, granulated using a solution of the polyvinylpyrrolidone in isopropyl alcohol, and dried. The granule is blended with magnesium stearate and silcon dioxide, and filled into hard gelatin capsules of a suitable size using conventional capsule filling machinery.

| Example 7 | mg/capsule |
| --- | --- |
| Active ingredient | 400.0 |
| Anhydrous sodium carbonate USNF | 25.0 |
| Microcrystalline cellulose | 72.5 |
| Silicon dioxide | 2.5 |
| Fill weight | 500.0 |

The microcrystalline cellulose and silicon dioxide are blended to form a pre-blend. This in turn is blended with the active ingredient and sodium carbonate. The resulting blend is filled into hard gelatin capsules of a suitable size using conventional capsule filling machinery.

| Example 8 | mg/tablet |
| --- | --- |
| Active ingredient | 800.0 |
| Anhydrous Sodium Carbonate USNF | 46.0 |
| Microcrystalline Cellulose Ph. Eur | 46.0 |
| Polyvinylpyrrolidone | 18.4 |
| Magnesium Stearate | 9.2 |
| | 918.6 |

The active ingredient, sodium carbonate and microcystalline cellulose were blended together, granulated with a solution of the polyvinylpyrrolidone in a mixture of isopropyl alcohol and water (90:10) and dried. The granule was blended with magnesium stearate and compressed into tablets using suitable punches.

| Example 9 | mg/tablet |
|---|---|
| Active ingredient | 750.0 |
| Sodium Carbonate | 45.0 |
| Lactose | 78.0 |
| Polyvinylpyrrolidone | 18.0 |
| Magnesium Stearate | 9.0 |
| | 900.0 |

The active ingredient, sodium carbonate and lactose are blended together, granulated using a solution of polyvinylpyrrolidone in isopropyl alcohol and dried. The granule is blended with magnesium stearate and compressed into tablets using suitable punches.

We claim:

1. A pharmaceutical composition in tablet form which weighs from about 400 to about 900 mg, said composition comprising a salt formed between ranitidine and a complex of bismuth with a carboxylic acid selected from the group consisting of tartaric acid and citric acid, mixed with an effective amount of from 2 to 8% w/w of an alkaline salt, wherein the amount of alkaline salt is effective to increase the rate of disintegration and dissolution of said composition after swallowing by a patient, and wherein the alkaline salt is selected from the group consisting of carbonates, bicarbonates, citrates and acetates.

2. A composition according to claim 1, containing from 200 to 800 mg of ranitidine bismuth carboxylate per unit dose.

3. A composition according to claim 1, containing from 50 to 95% w/w of ranitidine bismuth carboxylate.

4. A composition according to claim 1, in which said salt of ranitidine is selected from the group consisting of: N-[2-[[[5-[(dimethylamino)methyl]-2-furanyl]methyl]thio]ethyl]-N'-methyl-2-nitro-1, 1-ethenediamine 2-hydroxy-1,2, 3-propanetricarboxylate bismuth (3$^+$) complex; and N-[2-[[ 5-[(dimethylamino)methyl]-2-furanyl] methyl]thio]ethyl]-N'-methyl-2-nitro-1, 1-ethenediamine [R-(R*R*)]-2, 3-dihydroxybutanedioate bismuth (3$^+$) complex.

5. A composition according to claim 1, in which said alkaline salt is selected from the group consisting of alkali metal and alkaline earth metal carbonates and bicarbonates and mixtures thereof.

6. A composition according to claim 1, in which said alkaline salt is selected from the group consisting of sodium carbonate, sodium bicarbonate and mixtures thereof.

7. A composition according to claim 1, in which said ranitidine bismuth carboxylateisN-[2-[[[5-[(dimethylamino)methyl]-2-furanyl] methyl]thio]ethyl]-N'-methyl-2-nitro-1, 1-ethenediamine 2-hydroxy-1,2,3-propanetricarboxylate bismuth (3$^+$) complex and said alkaline salt is sodium carbonate.

8. A composition according to claim 1, also containing one or more physiologically acceptable carriers or excipients.

9. A composition according to claim 1 in which said ranitidine bismuth carboxylateisN-[2-[[[5-[(dimethylamino)methyl]-2-furanyl] methyl]thio]ethyl]-N'-methyl-2-nitro-1, 1-ethenediamine-2-hydroxy-1,2,3-propanetricarboxylate bismuth (3$^+$) and said alkaline salt is sodium carbonate.

10. A composition according to claim 1 which contains about 5% by weight of the alkaline salt.

11. A composition according to claim 10 which contains about 400 mg of ranitidine bismuth citrate.

* * * * *